(12) United States Patent
Qin et al.

(10) Patent No.: US 7,994,384 B2
(45) Date of Patent: Aug. 9, 2011

(54) ABSORBENT COMPOSITION HAVING MULTIPLE SURFACE TREATMENTS

(75) Inventors: Jian Qin, Appleton, WI (US); Hoa La Wilhelm, Appleton, WI (US); Sheng-Hsin Hu, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1089 days.

(21) Appl. No.: 10/833,501

(22) Filed: Apr. 28, 2004

(65) Prior Publication Data

US 2005/0256468 A1 Nov. 17, 2005

(51) Int. Cl.
*A61F 13/15* (2006.01)

(52) U.S. Cl. ............................................ 604/368
(58) Field of Classification Search .................... 604/368
See application file for complete search history.

(56) References Cited

U.S. PATENT DOCUMENTS

| | | | |
|---|---|---|---|
| 4,190,563 A * | 2/1980 | Bosley et al. ............... 523/111 |
| 4,500,670 A | 2/1985 | McKinley et al. | |
| 4,734,478 A | 3/1988 | Tsubakimoto et al. | |
| 4,824,901 A | 4/1989 | Alexander et al. | |
| 5,070,168 A | 12/1991 | O'Lenick, Jr. | |
| 5,230,959 A * | 7/1993 | Young et al. ............... 428/372 |
| 5,489,469 A | 2/1996 | Kobayashi et al. | |
| 5,625,015 A | 4/1997 | Brinen et al. | |
| 5,633,316 A | 5/1997 | Gartner et al. | |
| 5,716,707 A * | 2/1998 | Mukaida et al. ............ 428/402 |
| 5,800,418 A | 9/1998 | Ahr | |
| 5,868,724 A * | 2/1999 | Dierckes et al. ............ 604/368 |
| 6,387,495 B1 * | 5/2002 | Reeves et al. ............... 428/402 |
| 6,391,453 B1 | 5/2002 | Hansen et al. | |
| 6,596,402 B2 * | 7/2003 | Soerens et al. .............. 428/447 |
| 6,653,274 B1 * | 11/2003 | Godfroid et al. ............ 510/499 |
| 6,689,115 B1 | 2/2004 | Popp et al. | |
| 6,689,934 B2 * | 2/2004 | Dodge et al. ................ 604/367 |
| 6,824,650 B2 * | 11/2004 | Lindsay et al. ............ 162/168.2 |
| 6,849,665 B2 * | 2/2005 | Frenz et al. ................... 521/64 |
| 7,179,851 B2 * | 2/2007 | Qin et al. ..................... 523/200 |
| 7,396,584 B2 * | 7/2008 | Azad et al. ................... 428/327 |
| 2002/0150761 A1 * | 10/2002 | Lange et al. ................. 428/407 |
| 2003/0139717 A1 * | 7/2003 | Qin et al. ..................... 604/369 |
| 2004/0214499 A1 * | 10/2004 | Qin et al. ..................... 442/414 |

(Continued)

FOREIGN PATENT DOCUMENTS

EP 1 393 757 3/2004

(Continued)

OTHER PUBLICATIONS

International Search Report for WO 99/30751; WO "9930751_ISR. pdf", 4 pages.*

(Continued)

*Primary Examiner* — Melanie J Hand
*Assistant Examiner* — Ginger T Chapman
(74) *Attorney, Agent, or Firm* — Armstrong Teasdale LLP (57) ABSTRACT

An absorbent composition includes absorbent material, such as superabsorbent material, surface-treated with at least two different compatible agents. The superabsorbent material may be coated with multiple surface treatment agents in such a manner that each of the surface treatment agents is exposed on a surface of the superabsorbent material. For example, one surface treatment agent may be in a liquid coating form and another surface treatment agent may be in a powder form, each applied separately to the superabsorbent material.

27 Claims, 5 Drawing Sheets

U.S. PATENT DOCUMENTS

2005/0027268 A1* 2/2005 Qin et al. .................. 604/367
2005/0043696 A1* 2/2005 Schmidt et al. ............. 604/372
2005/0256469 A1* 11/2005 Qin et al. .................. 604/358

FOREIGN PATENT DOCUMENTS

| WO | WO 95/22357 | | 8/1995 |
| --- | --- | --- | --- |
| WO | WO 99/25393 | * | 5/1999 |
| WO | WO 99/30751 | * | 6/1999 |
| WO | 99/38541 | | 8/1999 |
| WO | 03/043670 | | 5/2003 |

OTHER PUBLICATIONS http://en.wikipedia.org/wiki/Polyethylene_glycol, viewed Aug. 27, 2009.

Office action received in corresponding Mexican Patent Application No. PA/a/2006/012307 (Aug. 20, 2009) (English translation).

European Office action regarding European Patent Application No. 05711478.7, dated Jan. 14, 2010.

* cited by examiner

ABSORBENT COMPOSITION HAVING MULTIPLE SURFACE TREATMENTS

BACKGROUND OF THE INVENTION

Personal care manufacturers are making thinner and more discreet products for consumers while, at a minimum, maintaining the product overall performance. This requires manufacturers to use higher amounts of superabsorbent materials (SAM), also known as absorbent gelling materials, and less pulp fibers than they have with conventional products.

Products with a high content of superabsorbent material tend to experience problems that are not encountered in products with low superabsorbent content. One such issue is poor superabsorbent containment. For example, in an absorbent core having a high quantity of SAM and a low amount of fibers, there may be insufficient fibers to hold or capture the SAM in the structure and to prevent the SAM from falling outside the core. This poor SAM containment issue could happen with structures having high SAM content under both dry and wet conditions. As an additional issue, poor structure integrity may lead to gel blocking. Gel blocking can be seen as a phenomenon in which SAMs pack themselves in the interstitial spaces in the core structure as the SAMs undergo rearrangements or deformation due to external forces from a wearer. This rearrangement of the SAM can result in lack of void volume available in the absorbent core, which can lead to poor intake of bodily fluid.

Manufacturers have been attempting to resolve these issues by incorporating thermoplastic binder fibers or hot melt adhesive in absorbent core structures to provide some attachment between SAMs or SAMs and fibers. These approaches may restrict the swelling of the SAMs and, thus, reduce the overall absorbency performance of the absorbent core. Also, these approaches often require use of large amounts of binder fibers and/or adhesives to sufficiently hold the structure together, which may undesirably result in increased stiffness of the absorbent pad.

There is thus a need, or desire, for a superabsorbent material that is capable of providing both wet and dry adhesion. There is a further need, or desire, for an absorbent pad that is thin and has good wet and dry structure integrity without compromising its absorbency performance. There is yet a further need, or desire, for a method of coating superabsorbent materials to achieve a superabsorbent material that is capable of delivering multiple functions.

SUMMARY OF THE INVENTION

The invention includes an absorbent material that is surface-treated or coated with at least two different agents such that the agents are compatible. These agents are herein referred to interchangeably as "agents" and "surface treatment agents." An example is a superabsorbent material coated with two different agents both of which are exposed on a surface of the superabsorbent material. As another example, at least one of the surface treatment agents is of opposing charge to that of the superabsorbent material, and at least one of the other surface treatment agents is a bonding agent. In a further example, at least one of the surface treatment agents can form an ionic charge opposite an ionic charge of the superabsorbent material. The superabsorbent material may be either cationic or anionic.

The surface treatment agents may include, but are not limited to, polyglycols, polyoxides, polyalcohols, modified celluloses, polyamines, polyquaternary ammoniums, polyimines, polycarboxylic acids, polyamides, polyesters, polyolefins, polystyrenes, polyurethanes, paraffin, wax, latex, and combinations thereof. For example, one of the surface treatment agents may include a hydrophilic thermoplastic material, such as polyethylene oxide.

One suitable surface treatment agent may include a water-soluble coating agent, such as polyvinyl amine (PVAm). Another suitable surface treatment agent applied to the same superabsorbent material may include a bonding agent. The bonding agent may be water-soluble, water-insoluble, or water-dispersible, and either thermoplastic or non-thermoplastic. Examples of suitable bonding agents include latex, polyethylene oxide, polypropylene oxide, polyethylene glycol, hydroxypropyl cellulose, modified starch, polyethylene, polyester, polyamide, polyvinyl alcohol, and/or copolymers or mixtures thereof.

For example, one surface treatment agent may be applied to the superabsorbent material in a liquid coating form, and another surface treatment agent may be applied to the superabsorbent material in a solid, partially dry, or dry particulate or powder form. For instance, the liquid coating agent may be applied to the superabsorbent material in a continuous film, and after the liquid coating has dried or partially dried, the superabsorbent material can be wetted as needed with an organic solvent, an aqueous solution, or water prior to applying the dry or partially dry powder. Alternatively, the superabsorbent material and the dry or partially dry powder may be combined in a coating chamber of a coating apparatus, into which a gaseous flow may be introduced while spraying a liquid coating agent into the coating chamber, thereby atomizing the liquid coating agent within the coating chamber.

In another example, the surface treatment agents may be combined in an emulsion and the emulsion may be applied to the superabsorbent material, thereby coating the superabsorbent material with both surface treatment agents in a single step. The emulsion solution may include a water-soluble coating agent, such as PVAm, and a water-dispersible adhesive, such as latex particles suspended in the PVAM solution. The emulsion of two separate phases can be introduced into a fluidized bed process to coat the superabsorbent material.

In yet another example, superabsorbent materials may be introduced into a fluidized coating chamber. A stream of PVAm solution and another separate stream of organic solvent containing water-soluble adhesive particles (or a separate stream of an aqueous solution containing water-insoluble or water-dispersible adhesive particles) may simultaneously or subsequently be atomized onto the surface of the superabsorbent materials.

The absorbent composition possesses wet stickiness, as determined by the Wet Stickiness Test, described below. The absorbent composition also possesses dry stickiness, as determined by the Thermal Stickiness Test, described below. The free swell gel bed permeability of the absorbent composition may be between about $50 \times 10^{-8}$ and about $500 \times 10^{-8}$ $cm^2$. The 0.3 psi swell gel bed permeability of the absorbent composition may be between about $10 \times 10^{-8}$ and about $50 \times 10^{-8}$ $cm^2$. The centrifuge retention capacity of the absorbent composition may be between about 20 and about 50 grams per gram.

With the foregoing in mind, it is a feature and advantage to provide absorbent compositions that possess multiple surface treatments and can thus deliver multiple attributes, as well as methods of coating superabsorbent material to achieve such absorbent compositions.

BRIEF DESCRIPTION OF THE DRAWINGS

These and other objects and features will be better understood from the following detailed description taken in conjunction with the drawings, wherein.

DEFINITIONS

Within the context of this specification, each term or phrase below will include the following meaning or meanings.

"Agents" or "surface treatment agents" comprise substances that do not form crosslinking, such as reacting with pendant functional groups of superabsorbent macromolecules to form "bridge" points between the polymer chains, upon, during, or at completion of the surface treatment or coating process.

"Compatibility" or "compatible" describes two or more surface treatment agents that, after coming into contact with each other and/or with a substrate which they coat, each maintains its individual original properties or functions and is able to deliver those functions/properties in use from the surface of the substrate or material which it coats.

"Hydrophilic" describes surfaces and fibers, or the surfaces of fibers, which have a high affinity for aqueous liquids and are wetted by the aqueous liquids when in contact with the surfaces. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System available from Thermo Electron Corporation in Madison, Wis., U.S.A., or a substantially equivalent system. When measured with this system, fibers or surfaces having contact angles of less than 90° are designated "wettable" or hydrophilic, while fibers or surfaces having contact angles greater than 90° are designated "nonwettable" or hydrophobic.

"Ionic-interaction-enhancing agent" refers to an agent having an ionic charge, or capable of forming an ionic charge, that is opposite an ionic charge of the material being treated or of other particles with which the agent comes in contact.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible configurational isomers of the material. These configurations include, but are not limited to isotactic, syndiotactic and atactic symmetries.

"Powder" includes materials in particulate form of any shape or size, including chopped fibers such as binder fibers.

"Superabsorbent" refers to a water-swellable, water-insoluble organic or inorganic material capable, under the most favorable conditions, of absorbing at least about 10 times its weight, or at least about 15 times its weight, or at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers. The superabsorbent material may be biodegradable or non-biodegradable. The superabsorbent materials can include particles, fibers, tows, flakes, films, foams, and the like. A material is "absorbent" if it absorbs at least five times its weight of the aqueous solution under these conditions.

"Surface" refers to an outermost or exterior boundary of a particle. The surface of a particle is that which is exposed to the atmosphere.

"Surface treatment" or "surface treating" refers to the application of an agent onto the surface of a particle, thereby covering at least a portion of the surface of the particle.

"Thermoplastic" is meant to describe a material that softens and/or flows when exposed to heat and which substantially returns to its original hardened condition when cooled to room temperature.

"Absorbent article" includes, but is not limited to, personal care absorbent articles, health/medical absorbent articles, and household/industrial absorbent articles.

"Personal care absorbent article" includes, but is not limited to, absorbent articles such as diapers, diaper pants, baby wipes, training pants, absorbent underpants, child care pants, swimwear, and other disposable garments; feminine care products including sanitary napkins, wipes, menstrual pads, menstrual pants, panty liners, panty shields, interlabials, tampons, and tampon applicators; adult-care products including wipes, pads, containers, incontinence products, and urinary shields; clothing components; bibs; athletic and recreation products; and the like.

"Health/medical absorbent article" includes a variety of professional and consumer health-care products including, but not limited to, products for applying hot or cold therapy, medical gowns (i.e., protective and/or surgical gowns), surgical drapes, caps, gloves, face masks, bandages, wound dressings, wipes, covers, containers, filters, disposable garments and bed pads, medical absorbent garments, underpads, and the like.

"Household/industrial absorbent articles" include construction and packaging supplies, products for cleaning and disinfecting, wipes, covers, filters, towels, disposable cutting sheets, bath tissue, facial tissue, nonwoven roll goods, home-comfort products including pillows, pads, cushions, masks and body care products such as products used to cleanse or treat the skin, laboratory coats, cover-alls, trash bags, stain removers, topical compositions, laundry soil/ink absorbers, detergent agglomerators, lipophilic fluid separators, and the like.

These terms may be defined with additional language in the remaining portions of the specification.

DESCRIPTION OF PREFERRED EMBODIMENTS

In accordance with the invention, absorbent compositions having multiple surface treatments are provided for use in a variety of absorbent articles. Absorbent articles containing these absorbent compositions are also provided. A method of making these absorbent compositions is also provided.

Absorbent materials treated with multiple surface treatment agents typically result in just one of the agents being exposed on the surface of the absorbent material. For example, if the surface treatment agents are not compatible, the effect of each surface treatment agent may be reduced or even eliminated. The compatibility of multiple surface treatment agents may depend on either or both the chemistry and the structural arrangement of the surface treatment agents. For example, the surface treatment agents are non-reactive with each other in order to be chemically compatible. As another example, the surface treatment agents are located in a suitable structural arrangement in order for each of the surface treatment agents to deliver their respective functions.

Some absorbent compositions consistent with the invention are designed to include multiple surface treatment agents on a superabsorbent material with each of the surface treatment agents exposed on the surface of the superabsorbent material. The surface treatment agents are chemically compatible with one another and/or are structurally arranged in such a way that each surface treatment agent is able to deliver its respective function.

Figure 1:
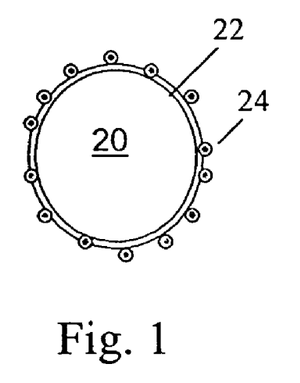
FIGS. 1 and 2 are diagrams of superabsorbent materials having multiple surface treatments and having the functionality of multiple surface treatments.
Figure 2:
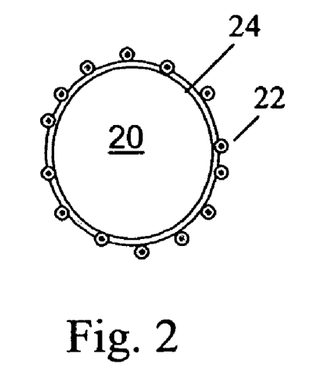

As shown in FIGS. 1 and 2, the superabsorbent material 20 can include a first surface treatment agent 22 and a second surface treatment agent 24, and both treatment agents are exposed on the surface of the superabsorbent material 20. Additional surface treatment agents may be included, but for simplicity, the figures herein illustrate just two surface treatment agents. The figures are used merely for illustration purposes, and there is no intention to limit the structure or morphology of the invention to the treated superabsorbent materials illustrated in the accompanying figures. The two agents can be either continuous/discontinuous, or discontinuous/discontinuous, or any discontinuous shapes as long as both of the agents are exposed on the surface.

Figure 3:
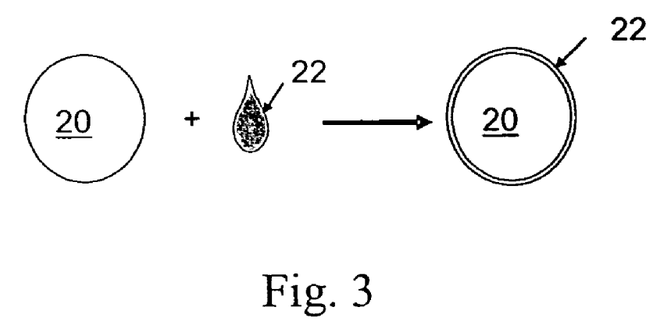
FIGS. 3 and 4 are diagrams of superabsorbent materials having single surface treatments.
Figure 4:
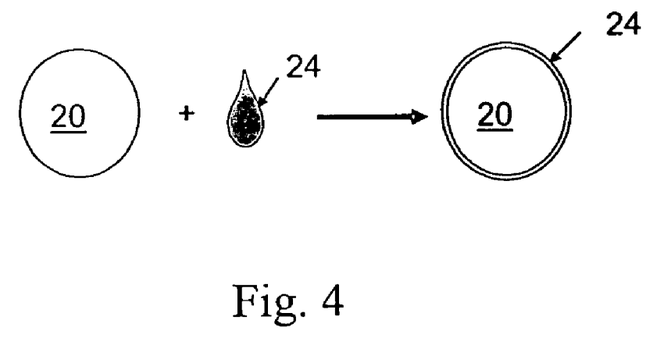

Typically when a single surface treatment agent, such as the first surface treatment agent 22 or the second surface treatment agent 24, is applied alone, the single surface treatment agent coats the superabsorbent material 20, as shown in FIGS. 3 and 4.

Figure 5:
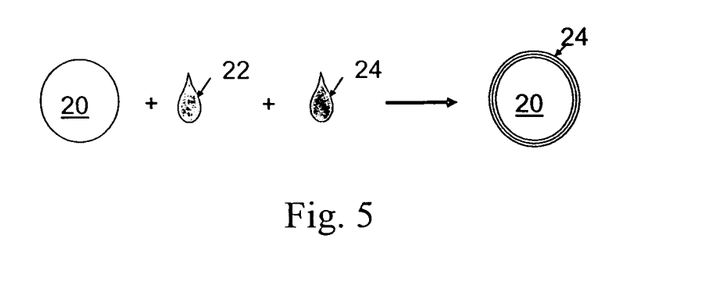
FIGS. 5-8 are diagrams of superabsorbent materials treated with multiple surface treatments but having the functionality of a single surface treatment.
Figure 6:
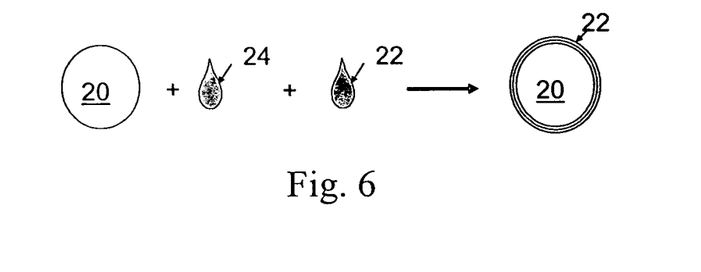

When two surface treatment agents are used and both of the surface treatment agents require application on the outermost surface of the superabsorbent material, the manner of applying the two surface treatment agents in order to have the agents be compatible needs some consideration. If a first surface treatment agent 22 is simply continuously applied to a superabsorbent material 20 followed by the application of a second surface treatment agent 24 also in a continuous coating, the resulting superabsorbent material 20 displays the characteristics of just the latter-applied surface treatment agent 24, as shown in FIG. 5. Likewise, when the second surface treatment agent 24 is applied first, the resulting superabsorbent material 20 may display the characteristics of just the latter-applied first surface treatment agent 22, as shown in FIG. 6.

Figure 7:
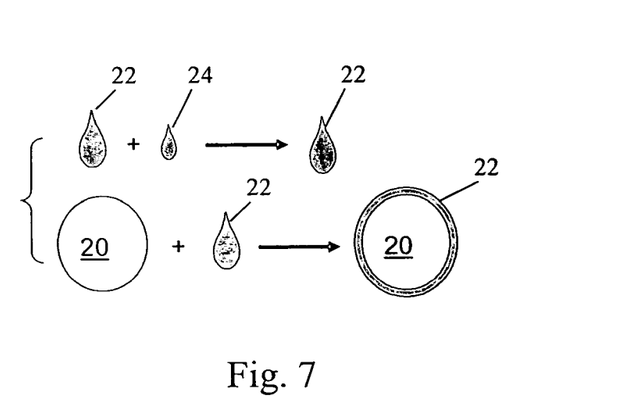
Figure 8:
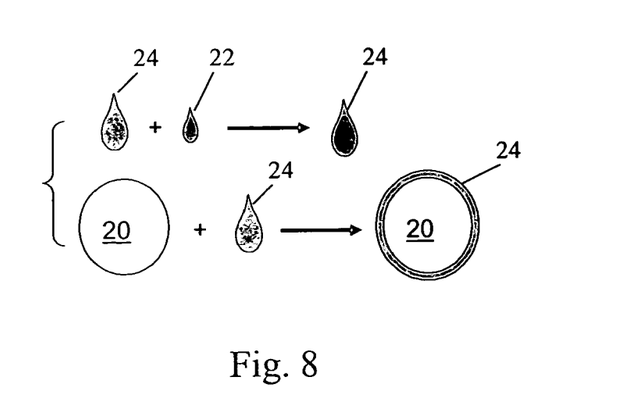

When the first and second surface treatment agents 22, 24 are mixed prior to applying the surface treatment agents to the superabsorbent material 20, the surface treatment agents 22, 24 may compete with one another and the properties of one of the surface treatment agents, such as the one of greater volume, may dominate the surface of the superabsorbent material 20, as shown in FIGS. 7 and 8.

The following methods and configurations are examples of achieving multiple surface treatment agents on a superabsorbent material with each of the surface treatment agents exposed on the surface of the superabsorbent material, as illustrated in FIGS. 1 and 2. The terms "first surface treatment agent" and "second surface treatment agent" are used interchangeably, with separate terms being used merely to indicate that at least two different surface treatment agents are present.

Figure 9:
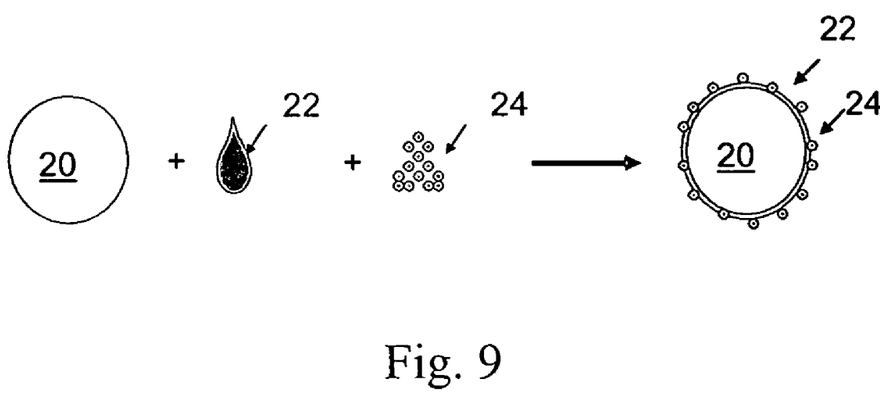
FIG. 9 is a diagram of superabsorbent material treated with multiple surface treatments and having the functionality of multiple surface treatments.

For example, a first surface treatment agent 22 can be applied to the superabsorbent material 20 as a liquid coating, using a conventional continuous or discontinuous coating process. A second surface treatment agent 24 can then be applied in a dry powder form in a discontinuous manner over the first surface treatment agent 22 using a dry powder surface coating process, resulting in a structure as shown in FIG. 9. The second surface treatment agent 24 such as the powder can be applied to the superabsorbent material 20 coated with the first surface treatment agent 22 by, for example, wetting the first surface treatment coating 22 on the superabsorbent surface with water or aqueous solution or the like and attaching the powder to the first surface treatment agent 22 in a discontinuous pattern, or by suspending/mixing the powder in water or aqueous solution or the like and applying, such as by spraying or mixing, the powder solution mixture over the first surface treatment agent 22 coating, or by at least partially wetting the powder with water or aqueous solution or the like and attaching the at least partially wet powder to the first surface treatment agent 22 coating on the superabsorbent surface. In order to keep the second surface treatment agent 24 from dissolving during the coating process, if it is water-soluble, a small amount of organic solvent (about 30% or less by weight of the second surface treatment agent) or a mixture of water and an organic solvent can be used. Examples of suitable organic solvents include acetone, methanol, ethanol, isopropanol, ethylene glycol, and propylene glycol. Alternatively, the second surface treatment agent 24 may be a water-insoluble, thermoplastic powder, in which case there is no need for concern regarding any dissolving issues during the coating process. Examples of suitable water-insoluble thermoplastic powders include polyethylene, polypropylene, polystyrene, polyester, polyamide, polyvinyl alcohol, polyurethane, wax, paraffin, and combinations thereof.

In some examples, one of the surface treatment agents may be a hydrophilic or water-soluble, thermoplastic polymer, such as polyethylene oxide, polypropylene oxide, hydroxypropyl cellulose, polyethylene imine, polyvinyl alcohol, or polyethylene glycol. Surface treatment agents of this type tend to cause superabsorbent materials to stick together upon heating, resulting in thermal stickiness, which is described in greater detail below. Such stickiness can be used to improve superabsorbent particle containment within an absorbent product, and can also reduce gel-on-skin issues.

In another example, two (or more) surface treatment agents may be applied to the superabsorbent material in a single-step process. Dry superabsorbent material and a first surface treatment agent in a dry powder form, such as polyethylene oxide powder, can be introduced into a coating chamber of a coating apparatus. A spray nozzle may be mounted at the center of the chamber. An inlet airflow may be adjusted to fluidize the superabsorbent material and the dry-powder first surface treatment agent. A second surface treatment agent in solution form, such as a polyvinyl amine solution, may be introduced through the nozzle and atomized into the chamber containing the fluidized superabsorbent material and dry-powder first surface treatment agent. The second surface treatment agent solution is atomized by the air in the chamber. The second surface treatment agent solution catches the dry-powder first surface treatment agent and adheres to the superabsorbent material.

A wide variety of fluidized bed coating systems can be adapted to coat superabsorbent materials with surface treatment agents. For example, one can use a Wurster Fluid Bed Coater such as the Ascoat Unit Model 101 of Lasko Co. (Leominster, Mass.), the Magnacoater® by Fluid Air, Inc. (Aurora, Ill.), or the modified Wurster coater described in U.S. Pat. No. 5,625,015, issued Apr. 29, 1997, to Brinen et al., which is hereby incorporated by reference in its entirety in a manner consistent with the present document. The coater is typically configured as a cylindrical or tapered vessel (larger diameter at the top than at the bottom) with air injection at the bottom through air jets or a distributor plate having multiple injection holes. Superabsorbent material and powder surface treatment agents are fluidized in the gaseous flow. One or more spray nozzles inject another coating material initially provided as a liquid, slurry, or foam at a point where good contact with the moving fibers and/or particles can be achieved. The superabsorbent material and powder surface treatment agent move upwards and descend behind a wall or barrier, from whence the particles can be guided to again enter the fluidized bed and be coated again, or can be removed and further processed. Elevated air temperature or the application of other forms of energy (microwaves, infrared radiation, electron beams, ultraviolet radiation, steam, and the like) causes drying or curing of the coating material on the fibers and/or particles. The superabsorbent material and powder surface treatment agent can be recycled through the fluidized bed a plurality of times to provide the desired amount of the other surface treatment agent on the superabsorbent material.

The surface treatment agents can be applied by many methods such as pan coating, spray coating, fluidized bed coating, and the like. The original Wurster fluid bed coaters are described in U.S. Pat. No. 2,799,241, issued Jul. 16, 1957, to D. E. Wurster; U.S. Pat. No. 3,089,824, issued May 14, 1963, to D. E. Wurster; U.S. Pat. No. 3,117,024, issued Jan. 7, 1964, to J. A. Lindlof et al.; U.S. Pat. No. 3,196,827, issued Jul. 27, 1965, to D. E. Wurster and J. A. Lindlof; U.S. Pat. No. 3,207,824, issued Sep. 21, 1965, to D. E. Wurster et al.; U.S. Pat. No. 3,241,520 issued Mar. 21, 1966, to D. E. Wurster and J. A. Lindlof; and U.S. Pat. No. 3,253,944, issued May 31, 1966, to D. E. Wurster; all of which are herein incorporated by reference in their entirety in a manner consistent with the present document. More recent examples of the use of Wurster coaters are given in U.S. Pat. No. 4,623,588, issued Nov. 18, 1986, to Nuwayser et al., which is hereby incorporated by reference in its entirety in a manner consistent with the present document. A related device is the coater of H. Littman disclosed in U.S. Pat. No. 5,254,168, "Coating Apparatus Having Opposed Atomizing Nozzles in a Fluid Bed Column," issued Oct. 19, 1993, which is hereby incorporated by reference in its entirety in a manner consistent with the present document.

The typical size of superabsorbent particles is around 150 microns to 800 microns. The surface treatment dry powder used in certain examples herein may be present as a finely divided solid, with particles smaller than 150 microns in maximum dimension.

In another example, the first and second surface treatment agents may be combined to form an emulsion by mixing or suspending one of the surface treatment agents, such as latex particles, in an oil phase and the other surface treatment agent, such as polyvinyl amine, in a water phase. The emulsion includes two separate phases, which can then be introduced into a coating apparatus, such as a fluidized bed coating system, to coat the superabsorbent material.

In order for all surface treatment agents to be exposed on the surface of the superabsorbent material as described in the examples above, only one of the surface treatment agents when they are both stable upon contact with bodily wastes, at most, may form a continuous film or layer on the surface of the treated superabsorbent. The second surface treatment agent has to be formed in a discontinuous fashion on top of the continuous or discontinuous layer of the first surface treatment agent.

For example, a first surface treatment agent may be an ionic-interaction enhancing agent and a second surface treatment agent may be a thermally sticky agent. An ionic-interaction-enhancing agent can form an ionic charge opposite an ionic charge of the superabsorbent material, and a thermally sticky agent is a thermoplastic material capable of becoming sticky when it is exposed to a temperature higher than its melting or softening temperature. The first surface treatment agent can be applied to the surface of the superabsorbent material continuously first, since ionic-interaction enhancing agents tend to promote inter-particle interaction or attraction when the treated particles are wet, and the second surface treatment agent can then be applied on top of the first surface treatment agent discontinuously. Furthermore, both the ionic-interaction-enhancing agent and the thermally sticky agent should be on the outermost surface of the superabsorbent material in order to deliver inter-particle attraction when wet and to form inter-particle bonds upon heating to provide dry structure integrity. If these two surface treatment agents were both applied continuously, the second surface treatment agent would obscure the first surface treatment agent's functional attributes, and only the second surface treatment agent would be functional.

Examples of suitable thermally sticky agents include polyethylene oxide, polypropylene oxide, hydroxypropyl cellulose, polyethylene imine, polyvinyl alcohol, polyethylene glycol, polyethylene, polyacrylate, polystyrene, polyamide, and combinations thereof. Examples of surface treatment agents having an opposite charge to that of the superabsorbent materials, also known as ionic-interacting-enhancing agents, include linear cationic polymers and linear anionic polymers. The ionic-interacting-enhancing agent does not cause a significant reduction in absorbent capacity and, in addition, may enhance inter-particle interaction after the treated superabsorbent material is wet. The inter-particle interaction may be so strong that it causes particles to stick together due to inter-particle ionic attraction, since the surface of the treated superabsorbent material contains both cationic and anionic regions in a swollen state. The ionic interaction may improve the wet integrity of the superabsorbent material and may significantly enhance the fluid permeability and intake function of the superabsorbent material due to the generation of air pockets caused by a combination of superabsorbent material swelling and formation of inter-particle ionic bonds.

The surface treatment agents may include bonding agents or coating agents, either water-soluble, water-insoluble, or water-dispersible. In general, examples of suitable surface treatment agents include polyglycols, such as polyethylene glycol, polypropylene glycol, polyethylene-propylene glycol copolymer; polyoxides, such as polyethylene oxide, polypropylene oxide, polyethylene-propylene oxide copolymer; polyalcohols, such as polyvinyl alcohol, polyvinyl alcohol copolymer; modified celluloses, such as hydroxypropyl cellulose, hydroxyethyl cellulose, methyl ethyl cellulose; polyquaternary ammoniums, such as polydiallyl dimethyl ammonium hydroxide; polyamines, such as polyvinyl amine; polyimines, such as polyethylene imine; polycarboxylic acids, such as polyacrylic acid, carboxymethyl cellulose; polyamides, such as polycaproamide; polyesters, such as polymethyl methacrylate, polytetramethylene terephthalate; polyolefins, such as polyethylene, polypropylene; polystyrenes; polyurethanes; paraffin; wax; latex; and mixtures or copolymers of all the above, such as polyacrylic acid-methyl methacrylate copolymer, polyacrylic acid-polyethylene copolymer, and the like. Two or more of these surface treatment agents, when used in combination as described herein, should be chemically compatible with one another and/or structurally arranged in such a way that each surface treatment agent is able to deliver its respective function.

One example of a suitable first surface treatment agent is polyvinyl amine solution, available from BASF Corporation in Mount Olive, N.J., under the trade name CATIOFAST® PR8106 (23 wt % solids). The polyvinyl amine solution can be dissolved in distilled water, to which the superabsorbent material may be added and stirred. After swelling, the superabsorbent material can be dried, such as at about 60 degrees Celsius for about 15 hours or longer. The dried superabsorbent material can be ground and screened through a sieve.

One example of a suitable second surface treatment agent is polyethylene oxide powder, available from Union Carbide in Danbury, Conn., under the trade name POLYOX® 205. The powder can be attached or coated to the surface of the superabsorbent material over the first surface treatment agent via water or an aqueous solution comprising an organic solvent such as an isopropyl alcohol/water mixture.

The surface-treated superabsorbent material suitably contains between about 0.01% and about 10%, or between about 0.1% and about 5% by weight of each of the surface treatment agents. In certain examples, equal amounts of each of the surface treatment agents may be applied to the superabsorbent material, however, an even ratio is not required.

It is also contemplated that a superabsorbent material may be coated or surface treated with at least two different agents wherein the outermost agent coating is a continuous layer. Under certain conditions, such as upon contact with bodily waste or fluid, the outermost layer or coating at least partially dissolves or disperses to unveil at least a portion of the underlying agent coating.

It is also contemplated that a superabsorbent material may be coated or surface treated with at least two different agents wherein the first agent forms a continuous layer and the second agent forms a discontinuous coating on top of the continuous layer of the first agent. An additional substance, distinct from at least the second agent, may be applied to the treated superabsorbent material to form either a continuous layer over both the first and second agents, or a discontinuous layer that partially covers the first and/or second agents. For example, the additional substance in combination with a discontinuous layer of the second surface treatment agent may form a continuous layer over the first surface treatment agent. The additional substance may be an inert material, which may partially or fully dissolve or disperse upon contact with bodily wastes to unveil at least a portion of the underlying coating agent or agents.

The superabsorbent materials can include particulates, flakes, fibers, films, foams, non-ionic superabsorbents, and/or ionic superabsorbents, sodium polyacrylate superabsorbents, for example. The superabsorbent materials can be selected from natural, synthetic, and modified natural polymers and materials. The superabsorbent materials can be inorganic materials, such as silica gels, or organic compounds, such as crosslinked polymers. Conventional superabsorbent materials are crosslinked polyelectrolytes. Polyelectrolytes include either anionic or cationic polymers. Anionic polymers contain functional groups such as carboxyl, sulfonate, sulphate, sulfite, phosphate, or a mixture thereof. Examples of anionic polymers include, but are not limited to, salts or partial salts of polyacrylic acid, polyacrylamido methylpropane sulfonic acid, polyvinyl acetic acid, polyvinyl phosphonic acid, polyvinyl sulfonic acid, isobutylene-maleic anhydride copolymer, carboxymethyl cellulose, alginic acid, carrageenan, polyaspartic acid, polyglutamic acid, and copolymers or mixtures thereof. Cationic polymers contain functional groups such as primary, secondary, and tertiary amine, imine, amide, quaternary ammonium, or mixtures thereof. Examples of cationic polymers include, but are not limited to, salts or partial salts of polyvinyl amine, polydiallyl dimethyl ammonium hydroxide, polyacrylamidopropyl trimethyl ammonium hydroxide, polyamino propanol vinyl ether, polyallylamine, chitosan, polylysine, polyglutamine, and copolymers or mixtures thereof. Examples of commercially available superabsorbent materials include SXM 9394, SXM 9543, and FAVOR 880, each available from Degussa Superabsorber in Greensboro, N.C., U.S.A., and Dow DRYTECH 2035HP, available from Dow Chemical Co. in Midland, Mich., U.S.A. These and other superabsorbent materials, including biodegradable superabsorbents, are suitable for use in the absorbent compositions. The superabsorbent material may include pre-screened 300-600 micron particles.

The term "polymer," as used herein, refers to either a single polymer or to a mixture of polymers. The term "anionic polymer," as used herein, refers to a polymer or mixture of polymers including a functional group or groups having a potential for becoming negatively charged ions upon ionization in an aqueous solution. The term "cationic polymer," as used herein, refers to a polymer or mixture of polymers including a functional group or groups having a potential for becoming positively charged ions upon ionization in an aqueous solution.

The absorbent compositions including the superabsorbent material having multiple surface treatments may have considerable absorbent capacity and gel strength. Gel strength of the superabsorbent material is assessed herein using 0.3 psi pressure swell gel bed permeability (GBP), described in detail in the Test Methods section below. The surface-treated superabsorbent material included in the absorbent compositions described herein suitably has a 0.3 psi pressure swell GBP of about 10 to about 50 ($\times 10^{-8}$ cm$^2$), or about 20 to about 50 ($\times 10^{-8}$ cm$^2$), or about 30 to about 50 ($\times 10^{-8}$ cm$^2$). The surface-treated superabsorbent material included in the absorbent compositions suitably has a free swell gel bed permeability (GBP) of about 50 to about 500 ($\times 10^{-8}$ cm$^2$), or about 100 to about 500 ($\times 10^{-8}$ cm$^2$), or about 200 to about 500 ($\times 10^{-8}$ cm$^2$), as determined by the free swell GBP Test Method described in detail below, and a centrifuge retention capacity (CRC) between about 20 and about 50 grams/gram, or between about 25 and about 40 grams/gram, as determined by the CRC Test Method described in detail below. Additionally, in certain examples, the surface-treated superabsorbent material or absorbent composition may possess wet stickiness, as determined by the Wet Stickiness Test Method described in detail below. The absorbent composition may also possess thermal stickiness, as determined by the Thermal Stickiness Test Method described in detail below.

In addition to the superabsorbent material having multiple surface treatments, the invention may also include absorbent cores or absorbent composites containing the absorbent compositions, suitably in a concentration of up to about 100%, or about 65% or more, or about 85% or more by weight of the absorbent cores or composites. The absorbent composites may include between about 5% and about 35% by weight natural, modified natural, and/or synthetic fibers.

The fibers may include, but are not limited to, chemical pulps such as sulfite and sulfate (sometimes called Kraft) pulps, as well as mechanical pulps such as ground wood, thermomechanical pulp and chemithermomechanical pulp. For example, the pulp fibers may include cotton, typical wood pulps, cellulose acetate, rayon, thermomechanical wood pulp, chemical wood pulp, debonded chemical wood pulp, milkweed floss, and combinations thereof. Pulps derived from both deciduous and coniferous trees can be used. The fibers may also be elastomeric or thermal binder fibers. Additionally, the fibers may include such hydrophilic materials as microcrystalline cellulose, microfibrillated cellulose, or any of these materials in combination with wood pulp fibers.

A surfactant may also be added to the absorbent composite to increase its wettability, or hydrophilicity. Examples of suitable surfactants are commercially available from Uniqema in Wilmington, Del., under the trade designation AHCOVEL, and from Cognis Corporation in Cincinnati, Ohio, under the trade designation GLUCOPON 220.

The absorbent composite can be formed on a coform line. Coform processes combine separate polymer and additive streams into a single deposition stream in forming a nonwoven web. One example of such a process is disclosed in U.S. Pat. No. 4,100,324 to Anderson et al., which is hereby incorporated by reference in its entirety in a manner consistent with the present document. Another example of a suitable process for forming an absorbent composite is described in U.S. Pat. No. 5,350,624 to Georger et al., which is also hereby incorporated by reference in its entirety in a manner consistent with the present document. The polymers suitable for forming coform nonwoven webs include any thermoplastic materials. Examples include, but are not limited to, polyethylene, polypropylene, polyester, polyamide, polyurethane, and elastomeric thermoplastic materials, such as polyethylene elastomers, polypropylene elastomers, polyester elastomers, polyisoprene, cross-linked polybutadiene, diblock, triblock, or other multi-block thermoplastic elastomeric and/or flexible copolymers.

The invention may also include absorbent articles containing the absorbent composition. Examples of such suitable articles include personal care absorbent articles, such as diapers, diaper pants, baby wipes, training pants, absorbent underpants, child care pants, swimwear, sanitary napkins, wipes, menstrual pads, changing pads, menstrual pants, panty liners, panty shields, interlabials, tampons, tampon applicators, incontinence products, urinary shields, clothing components, bibs, shoe inserts, athletic and recreation products; health/medical absorbent articles such as products for applying hot or cold therapy, medical gowns (i.e., protective and/or surgical gowns), surgical drapes, caps, gloves, face masks, bandages, wound dressings, wipes, covers, containers, filters, disposable garments and bed pads, medical absorbent garments, underpads; household/industrial absorbent articles such as construction and packaging supplies, products for cleaning and disinfecting, wipes, covers, filters, towels, disposable cutting sheets, bath tissue, facial tissue, nonwoven roll goods, home-comfort products including pillows, pads, cushions, masks and body care products such as products used to cleanse or treat the skin, laboratory coats, cover-alls, trash bags, stain removers, topical compositions, laundry soil/ink absorbers, detergent agglomerators, lipophilic fluid separators; and the like. Absorbent composites consistent with the invention may be used in either a single layer structure or a multi-layer structure, such as in a dual layer structure wherein the absorbent composite may serve as the upper layer, the lower layer, or both layers.

Figure 10:
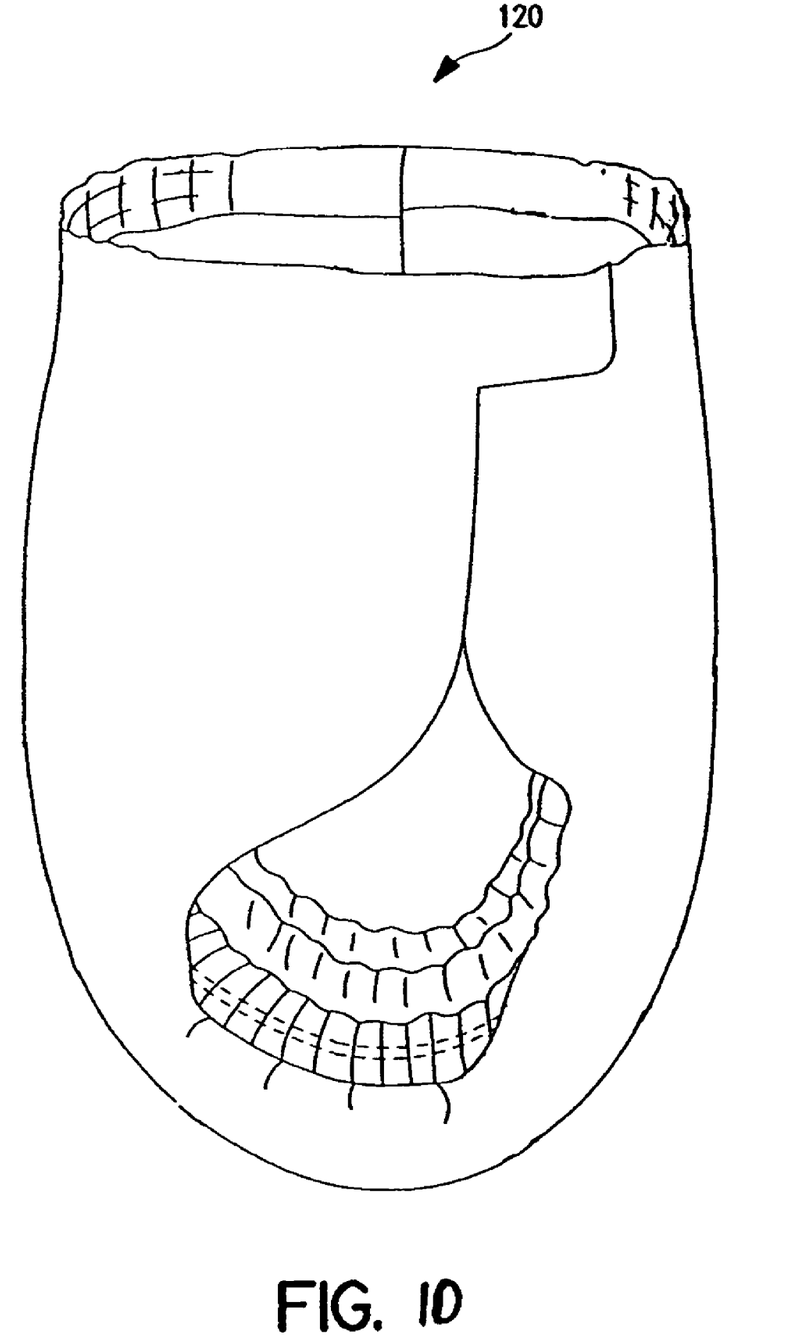
FIG. 10 is a perspective view of an absorbent article into which an absorbent composition may be incorporated.

An example of a suitable absorbent article 120 into which the absorbent composition may be incorporated is illustrated in FIG. 10, and described in detail in U.S. Pat. No. 6,689,115 issued Feb. 10, 2004, and incorporated herein by reference in its entirety in a manner consistent with the present document. For example, the absorbent composition may form all or part of an absorbent core positioned between an outer cover and a body side liner of an absorbent article. Because of the absorbent composition's stickiness, the absorbent composition may be used in an unwrapped state. More particularly, a tissue or other wrapping material may not be required to contain the absorbent composition.

Test Methods

Centrifuge Retention Capacity (CRC) Test

The Centrifuge Retention Capacity (CRC) Test measures the ability of the superabsorbent material to retain liquid therein after being saturated and subjected to centrifugation under controlled conditions. The resultant retention capacity is stated as grams of liquid retained per gram weight of the sample (g/g). The sample to be tested is prepared from particles which are prescreened through a U.S. standard 30 mesh screen and retained on a U.S. standard 50 mesh screen. As a result, the sample comprises particles sized in the range of about 300 to about 600 microns. The particles can be prescreened by hand or automatically and are stored in a sealed airtight container until testing.

The retention capacity is measured by placing 0.2±0.005 grams of the prescreened sample into a water-permeable bag which will contain the sample while allowing a test solution (0.9 weight percent sodium chloride in distilled water) to be freely absorbed by the sample. A heat-sealable tea bag material, such as that available from Dexter Corporation of Windsor Locks, Conn., U.S.A., as model designation 1234T heat-sealable filter paper works well for most applications. The bag is formed by folding a 5-inch by 3-inch sample of the bag material in half and heat-sealing two of the open edges to form a 2.5-inch by 3-inch rectangular pouch. The heat seals should be about 0.25 inches inside the edge of the material. After the sample is placed in the pouch, the remaining open edge of the pouch is also heat-sealed. Empty bags are also made to serve as controls. Three samples (e.g., filled and sealed bags) are prepared for the test. The filled bags must be tested within three minutes of preparation unless immediately placed in a sealed container, in which case the filled bags must be tested within thirty minutes of preparation.

The bags are placed between two TEFLON® coated fiberglass screens having 3 inch openings (Taconic Plastics, Inc., Petersburg, N.Y.) and submerged in a pan of the test solution at 23 degrees Celsius, making sure that the screens are held down until the bags are completely wetted. After wetting, the samples remain in the solution for about 30±1 minutes, at which time they are removed from the solution and temporarily laid on a non-absorbent flat surface. For multiple tests, the pan should be emptied and refilled with fresh test solution after 24 bags have been saturated in the pan.

The wet bags are then placed into the basket of a suitable centrifuge capable of subjecting the samples to a g-force of about 350. One suitable centrifuge is a Heraeus LaboFuge 400 having a water collection basket, a digital rpm gauge, and a machined drainage basket adapted to hold and drain the bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the samples. The amount of solution retained by the sample, taking into account the solution retained by the bag itself, is the centrifuge retention capacity (CRC) of the sample, expressed as grams of fluid per gram of sample. More particularly, the retention capacity is determined as:

$$\frac{\text{Sample \& bag weight after centrifuge} - \text{empty bag weight after centrifuge} - \text{dry sample weight}}{\text{dry sample weight}}$$

The three samples are tested and the results are averaged to determine the retention capacity (CRC) of the superabsorbent material. The samples are tested at 23±1 degrees Celsius at 50±2 percent relative humidity.

0.3 psi Pressure Swell Gel Bed Permeability (GBP)

As used herein, the Gel Bed Permeability (GBP) Under Load Test, otherwise referred to herein as 0.3 psi pressure swell GBP, determines the permeability of a swollen bed of gel particles under conditions that are commonly referred to as being "under load" conditions. The term "under load" means that swelling of the particles is restrained by a load generally consistent with normal usage loads applied to the particles, such as sitting, walking, twisting, etc. by the wearer.

Figure 11:
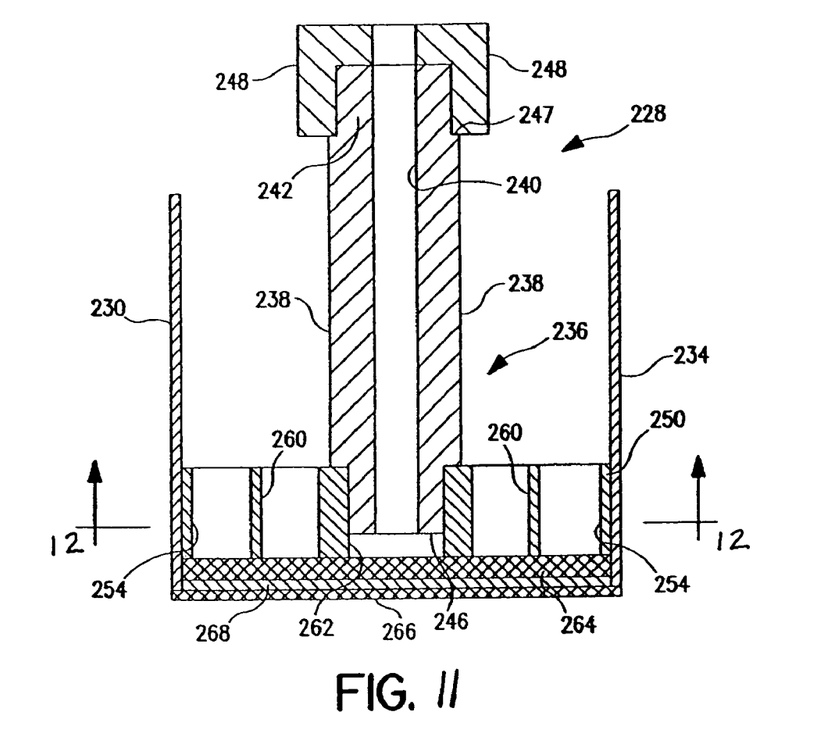
FIG. 11 depicts apparatus used to measure free swell or 0.3 psi swell permeability of either free-flowing particles or absorbent composites.
Figure 12:
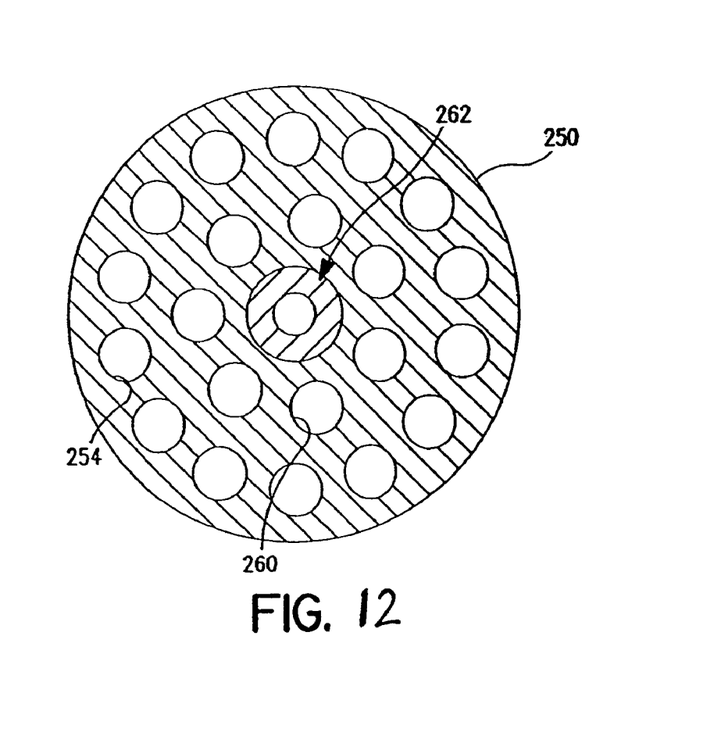
FIG. 12 depicts a bottom view of the apparatus of FIG. 11.

A suitable apparatus for conducting the Gel Bed Permeability Test is shown in FIGS. 11 and 12 and indicated generally at 228. The test apparatus 228 comprises a sample container, generally indicated at 230, and a piston, generally indicated at 236. The piston 236 comprises a cylindrical LEXAN shaft 238 having a concentric cylindrical hole 240 bored down the longitudinal axis of the shaft. Both ends of the shaft 238 are machined to provide upper and lower ends respectively designated 242, 246. A weight, indicated as 248, rests on one end 242 and has a cylindrical hole bored through at least a portion of its center.

A circular piston head 250 is positioned on the other end 246 and is provided with a concentric inner ring of seven holes 260, each having a diameter of about 0.95 cm, and a concentric outer ring of fourteen holes 254, also each having a diameter of about 0.95 cm. The holes 254, 260 are bored from the top to the bottom of the piston head 250. The piston head 250 also has a cylindrical hole 262 bored in the center thereof to receive end 246 of the shaft 238. The bottom of the piston head 250 may also be covered with a biaxially stretched 100 mesh stainless steel screen 264.

The sample container 230 comprises a cylinder 234 and a 400 mesh stainless steel cloth screen 266 that is biaxially stretched to tautness and attached to the lower end of the cylinder. A gel particle sample, indicated as 268 in FIG. 11, is supported on the screen 266 within the cylinder 234 during testing.

The cylinder 234 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of approximately 10 cm. Drainage holes (not shown) are formed in the sidewall of the cylinder 234 at a height of approximately 7.8 cm above the screen 266 to allow liquid to drain from the cylinder to thereby maintain a fluid level in the sample container at approximately 7.8 cm above the screen 266. The piston head 250 is machined from a LEXAN rod or equivalent material and has a height of approximately 16 mm and a diameter sized such that it fits within the cylinder 234 with minimum wall clearance but still slides freely. The shaft 238 is machined from a LEXAN rod or equivalent material and has an outer diameter of about 2.22 cm and an inner diameter of about 0.64 cm.

The shaft upper end 242 is approximately 2.54 cm long and approximately 1.58 cm in diameter, forming an annular shoulder 247 to support the weight 248. The annular weight 248 has an inner diameter of about 1.59 cm so that it slips onto the upper end 242 of the shaft 238 and rests on the annular shoulder 247 formed thereon. The annular weight 248 can be made from stainless steel or from other suitable materials resistant to corrosion in the presence of the test solution, which is 0.9 weight percent sodium chloride solution in distilled water. The combined weight of the piston 236 and annular weight 248 equals approximately 596 grams (g), which corresponds to a pressure applied to the sample 268 of about 0.3 pounds per square inch (psi), or about 20.7 dynes/cm$^2$ (2.07 kPa), over a sample area of about 28.27 cm$^2$.

When the test solution flows through the test apparatus during testing as described below, the sample container 230 generally rests on a 16 mesh rigid stainless steel support screen (not shown). Alternatively, the sample container 230 may rest on a support ring (not shown) diametrically sized substantially the same as the cylinder 234 so that the support ring does not restrict flow from the bottom of the container.

To conduct the 0.3 psi pressure swell Gel Bed Permeability Test, the piston 236, with the weight 248 seated thereon, is placed in an empty sample container 230 and the height is measured using a suitable gauge accurate to 0.01 mm with the platen removed. It is important to measure the height of each sample container 230 empty and to keep track of which piston 236 and weight 248 is used when using multiple test apparatus. The same piston 236 and weight 248 should be used for measurement when the sample 268 is later swollen following saturation.

The sample to be tested is prepared from particles which are prescreened through a U.S. standard 30 mesh screen and retained on a U.S. standard 50 mesh screen. As a result, the test sample comprises particles sized in the range of about 300 to about 600 microns. The particles can be prescreened by hand or automatically. Also test samples can be as-is particles. Approximately 2.0 grams of the sample are placed in the sample container 230 and spread out evenly on the bottom of the sample container 230. The sample container 230, with 2.0 grams of sample in it, and with the piston 236 and weight 248 placed on the sample within the sample container 230, is then submerged in the test solution for a time period of about 60 minutes to saturate the sample.

At the end of this period, the sample container 230, piston 236, weight 248, and sample 268 are removed from the solution. The thickness of the saturated sample 268 is determined by again measuring the height from the bottom of the weight 248 to the top of the cylinder 234, using the same thickness gauge used previously provided that the zero point is unchanged from the initial height measurement. The height measurement obtained from measuring the empty sample container 230, piston 236, and weight 248 is subtracted from the height measurement obtained after saturating the sample 268. The resulting value is the thickness, or height "H" of the swollen sample.

The permeability measurement is initiated by delivering a flow of the test solution into the sample container 230 with the saturated sample 268, piston 236, and weight 248 inside. The flow rate of test solution into the sample container 230 is adjusted to maintain a fluid height of about 7.8 cm above the bottom of the sample container 230. The quantity of solution passing through the sample 268 versus time is measured gravimetrically. Data points are collected every second for at least twenty seconds once the fluid level has been stabilized to and maintained at about 7.8 cm in height. The flow rate Q through the swollen sample 268 is determined in units of grams/second (g/s) by a linear least-square fit of fluid passing through the sample 268 (in grams) versus time (in seconds).

Permeability in cm$^2$ is obtained by the following equation:

$$K=[Q*H*\mu]/[A*\rho*P]$$

where K=Permeability (cm$^2$), Q=flow rate (g/sec), H=height of sample (cm), μ=liquid viscosity (poise) (approximately one centipoises for the test solution used with this Test), A=cross-sectional area for liquid flow (cm$^2$), ρ=liquid density (g/cm$^3$) (approximately one g/cm$^3$, for the test solution used with this Test) and P=hydrostatic pressure (dynes/cm$^2$) (normally approximately 3,923 dynes/cm$^2$). The hydrostatic pressure is calculated from $$P=\rho*g*h$$

where $\rho$=liquid density (g/cm$^3$), g=gravitational acceleration, nominally 981 cm/sec$^2$, and h=fluid height, e.g., 7.8 cm for the Gel Bed Permeability Test described herein.

A minimum of three samples is tested and the results are averaged to determine the gel bed permeability of the sample.

Free Swell Gel Bed Permeability (GBP)

As used herein, the Gel Bed Permeability (GBP) Under Free Swell Test, otherwise referred to herein as free swell GBP, determines the permeability of a swollen bed of gel particles under conditions that are commonly referred to as being "free swell" or "no load" conditions. The term "free swell" means that swelling of the particles is free without being restrained by an external load.

The free swell GBP test is substantially the same as the 0.3 psi pressure swell GBP test set forth above, with the following exception. After approximately 2.0 grams of the sample are placed in the sample container 230 and spread out evenly on the bottom of the sample container, the container, with 2.0 grams of sample in it, without the piston 236 and weight 248 therein, is then submerged in the test solution for a time period of about 60 minutes to saturate the sample and allow the sample to swell free of any restraining load. At the end of this period, the piston 236 and weight 248 assembly is placed on the saturated sample 268 in the sample container 230 and then the sample container 230, piston 236, weight 248, and sample 268 are removed from the solution. The thickness of the saturated sample 268 is determined by again measuring the height from the bottom of the weight 248 to the top of the cylinder 234, using the same thickness gauge used previously, provided that the zero point is unchanged from the initial height measurement. The rest of the test procedure is the same as that of the 0.3 psi pressure swell GBP test.

Wet Stickiness Test Method

To determine if a superabsorbent material is "wet sticky," the superabsorbent material is first sieved and 2 grams of 300 to 600 micron superabsorbent particles are poured into a 100 ml PYREX® glass beaker and then 5 grams of 0.9 wt % NaCl saline are added. If the particles stick together after the particles swell (determined by picking up the gel bed with one's fingers and more than 70%, suitably about 100%, of the swollen gels sticking together), then the superabsorbent material is considered to possess "wet stickiness."

Thermal Stickiness Test Method

To determine if a superabsorbent material is "thermally sticky," the superabsorbent material is first sieved and 5 grams of 300 to 600 micron superabsorbent particles are poured into a 100 ml PYREX® glass beaker. The glass beaker is then heated at a temperature above the melting or softening temperature of the thermoplastic surface treatment agent, for example, 150 degrees Celsius for hydroxypropyl cellulose, for 10 minutes and then completely cooled to room temperature (about 22 degrees Celsius). Once the beaker is cooled, the beaker is then turned upside-down. If less than about 30%, or less than about 1.5%, or 0%, by weight of the particles fall out of the beaker upon being turned upside-down, then the superabsorbent material is considered to possess "thermal stickiness."

EXAMPLE

In this example, eight samples of superabsorbent material were treated with various combinations of surface treatment agents. The samples were tested for absorbency and stickiness properties. The results are presented in Table 1.

Sample 0 was an untreated form of the same superabsorbent material used in Samples 1-8, namely SXM 9543, available from Degussa Superabsorber, Greensboro, N.C.

Sample 1 was prepared by combining 2.17 grams of polyvinyl amine aqueous solution, available from BASF under the trade name CATIOFAST® PR8106 at a solids level of 23 wt %, in a 250 ml glass beaker with 48.33 grams of distilled water. The mixture was stirred until a uniform solution was formed. While the solution was being vigorously stirred, 20 grams of the dry superabsorbent powder of Sample 0 were added to the solution. The superabsorbent powder absorbed all the solution, and the partially swollen superabsorbent particles were dried in an oven at 60 degrees Celsius for about 15 hours. The dried superabsorbent particles were pressed and sieved through 30 (600 microns) and 50 (300 microns) mesh sieves. The properties of the sieved particles between 300 and 600 microns are presented in Table 1. FIG. 3 is representative of Sample 1.

Sample 2 was prepared by combining 1 gram of polyethylene oxide powder, available from Union Carbide under the trade name POLYOX® 205, in a 250 ml glass beaker with 50 grams of distilled water. The mixture was stirred until a uniform solution was formed. While the solution was being vigorously stirred, 20 grams of the dry superabsorbent powder of Sample 0 were added to the solution. The superabsorbent powder absorbed all the solution, and the partially swollen superabsorbent particles were dried in an oven at 60 degrees Celsius for about 15 hours. The dried superabsorbent particles were pressed and sieved through 30 (600 microns) and 50 (300 microns) mesh sieves. The properties of the sieved particles between 300 and 600 microns are presented in Table 1. FIG. 4 is representative of Sample 2.

Sample 3 was prepared by combining 1 gram of polyethylene oxide powder, available from Union Carbide under the trade name POLYOX® 205, in a 250 ml glass beaker with 50 grams of distilled water. The mixture was stirred until a uniform solution was formed. While the solution was being vigorously stirred, 20.5 grams of polyvinyl amine surface-treated SXM 9543 prepared in the same way as described in Sample 1 were added into the POLYOX® solution. The superabsorbent material absorbed all the solution, and the swollen superabsorbent particles were dried in an oven at 60 degrees Celsius for about 15 hours. The dried superabsorbent particles were pressed and sieved through 30 (600 microns) and 50 (300 microns) mesh sieves. The properties of the sieved particles between 300 and 600 microns are presented in Table 1. FIG. 5 is representative of Sample 3.

Sample 4 was prepared by combining 2.17 grams of polyvinyl amine aqueous solution, CATIOFAST® PR8106, in a 250 ml glass beaker with 48.33 grams of distilled water. The mixture was stirred until a uniform solution was formed. While the solution was being vigorously stirred, 21 grams of polyethylene oxide surface-treated SXM 9543 prepared in the same way as described in Sample 2 were added into the CATIOFAST® PR8106 solution. The superabsorbent material absorbed all the solution, and the swollen superabsorbent particles were dried in an oven at 60 degrees Celsius for about 15 hours. The dried superabsorbent particles were pressed and sieved through 30 (600 microns) and 50 (300 microns) mesh sieves. The properties of the sieved particles between 300 and 600 microns are presented in Table 1. FIG. 6 is representative of Sample 4.

Sample 5 was prepared by combining 0.5 gram of polyethylene oxide powder (POLYOX® 205), 4.35 grams of polyvinyl amine solution (CATIOFAST® PR8106), and 50 grams of distilled water in a 250 ml glass beaker. The mixture was stirred until a uniform solution was formed. While the solution was being vigorously stirred, 20 grams of dry SXM 9543 superabsorbent powder were added into the solution. The superabsorbent material absorbed all the solution, and the partially swollen superabsorbent particles were dried in an oven at 60 degrees Celsius for about 15 hours. The dried superabsorbent particles were pressed and sieved through 30 (600 microns) and 50 (300 microns) mesh sieves. The properties of the sieved particles between 300 and 600 microns are presented in Table 1. FIG. 7 is representative of Sample 5.

Sample 6 was prepared by combining 2 grams of polyethylene oxide powder (POLYOX® 205), 1.1 grams of polyvinyl amine solution (CATIOFAST® PR8106), and 50 grams of distilled water in a 250 ml glass beaker. The mixture was stirred until a uniform solution was formed. While the solution was being vigorously stirred, 20 grams of dry SXM 9543 superabsorbent powder were added into the solution. The superabsorbent material absorbed all the solution, and the partially swollen superabsorbent particles were dried in an oven at 60 degrees Celsius for about 15 hours. The dried superabsorbent particles were pressed and sieved through 30 (600 microns) and 50 (300 microns) mesh sieves. The properties of the sieved particles between 300 and 600 microns are presented in Table 1. FIG. 8 is representative of Sample 6.

Sample 7 was prepared by obtaining 20.5 grams of dry polyvinyl amine surface-treated SXM 9543 prepared in the same way as described in Sample 1, and spraying the surface-treated superabsorbent material with water mist to a level of about 0.5 grams of water per gram of superabsorbent material. For example, 5 grams of water were sprayed onto 10 grams of dry superabsorbent particles. After addition of the water moisture the superabsorbent particles remained separatable and flowable. Next, 1 gram of dry polyethylene oxide powder (POLYOX® 205) was added to the partially wetted superabsorbent particles, and the combination was stirred to achieve a uniform and even distribution. The treated particles were dried in an oven at 60 degrees Celsius for 5 hours. The dried superabsorbent particles were pressed and sieved again through 30 (600 microns) and 50 (300 microns) mesh sieves. The properties of the sieved particles between 300 and 600 microns are presented in Table 1. FIG. 9 is representative of Sample 7.

Sample 8 was prepared by obtaining 20.5 grams of dry polyvinyl amine surface-treated SXM 9543 prepared in the same way as described in Sample 1, wetting the surface-treated superabsorbent material with about 2 grams of an isopropyl alcohol/water mixture (at a ratio of 3 to 1), and stirring the combination to achieve a uniform distribution. Next, 1 gram of dry polyethylene oxide powder (POLYOX® 205) was added to the wetted superabsorbent particles, and the combination was vigorously stirred to achieve a uniform and even distribution. The treated particles were dried in an oven at 60 degrees Celsius for about 5 hours. The dried superabsorbent particles were pressed and sieved again through 30 (600 microns) and 50 (300 microns) mesh sieves. The properties of the sieved particles between 300 and 600 microns are presented in Table 1. FIG. 9 is representative of Sample 8.

TABLE 1

Properties of Treated Superabsorbent Materials

| | Surface Treatment | | | Absorbency | | Stickiness | |
| --- | --- | --- | --- | --- | --- | --- | --- |
| | CATIOFAST | POLYOX® | CRC | Free Swell GBP | 0.3 psi Swell GBP | | |
| Sample | (wt %) | (wt %) | (g/g) | ($\times 10^{-8}$ cm$^2$) | ($\times 10^{-8}$ cm$^2$) | Wet | Thermal |
| 0 | 0 | 0 | 23 | 31.2 | 14.5 | No | No |
| 1 | 2.5 | 0 | 21 | 341.8 | 39.6 | Yes | No |
| 2 | 0 | 5 | 23 | 24.0 | | No | Yes |
| 3 | 2.5 | 5 | 22 | 51.3 | 12.5 | No | Yes |
| 4 | 2.5 | 5 | 21 | 103.7 | 27.7 | Yes | No |
| 5 | 5 | 2.5 | 22 | 135.5 | | Yes | No |
| 6 | 1.25 | 10 | 22 | 44.8 | | No | Yes |
| 7* | 2.5 | 5 | 21 | 145.3 | 28.6 | Yes | Yes |
| 8* | 2.5 | 5 | 21 | 138.2 | | Yes | Yes |

Note:
*An example of this invention

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent composition, comprising:
a superabsorbent material surface-treated with at least two different agents, wherein the at least two agents are compatible, at least one of the agents comprises a thermoplastic material, each of the at least two agents is exposed on a surface of the superabsorbent material, wherein a first of the at least two agents forms a continuous layer on the superabsorbent material, and wherein at least one of the agents is chosen from polyoxides, polycarboxylic acids, polyamides, polyesters, polyolefins, polystyrenes, polyurethanes, paraffin, wax, latex, and combinations thereof.

2. The absorbent composition of claim 1, wherein at least one of the agents can form an ionic charge opposite an ionic charge of the superabsorbent material.

3. The absorbent composition of claim 1, wherein the superabsorbent material is anionic.

4. The absorbent composition of claim 1, wherein the superabsorbent material is cationic.

5. The absorbent composition of claim 1, wherein the superabsorbent material is surface crosslinked before either of the at least two agents is applied to the superabsorbent material.

6. The absorbent composition of claim 1, wherein a first agent forms a continuous layer on the superabsorbent material, a second agent forms a discontinuous layer on top of the first agent, and an additional substance forms a discontinuous layer on top of the first agent such that the second agent and the additional substance together form a continuous layer on top of the first agent.

7. The absorbent composition of claim 1, wherein the surface-treated superabsorbent material has a free swell gel bed permeability between about $50 \times 10^{-8}$ and about $500 \times 10^{-8}$ $cm^2$.

8. The absorbent composition of claim 1, wherein the surface-treated superabsorbent material has a 0.3 psi swell gel bed permeability between about $10 \times 10^{-8}$ and about $50 \times 10^{-8}$ $cm^2$.

9. The absorbent composition of claim 1, wherein the surface-treated superabsorbent material has a centrifuge retention capacity between about 20 and about 50 grams per gram.

10. An absorbent article comprising the absorbent composition of claim 1.

11. An absorbent core comprising at least 65% by weight of the absorbent composition of claim 1.

12. An absorbent article comprising an outer cover, a body side liner, and the absorbent core of claim 11 positioned between the outer cover and the body side liner, wherein the absorbent core is unwrapped.

13. The absorbent composition of claim 1, wherein at least one of the agents comprises a water-soluble coating agent.

14. The absorbent composition of claim 13, wherein another of the at least two agents comprises at least one of the group consisting of a water-soluble bonding agent, a water-insoluble bonding agent, and a water-dispersible bonding agent.

15. The absorbent composition of claim 1, wherein at least one of the agents is applied in a liquid coating form and another of the at least two agents is applied in a powder form.

16. An absorbent composition, comprising:
a highly-surface-crosslinked anionic superabsorbent material;
a first treatment agent of polyvinyl amine applied to a surface of the superabsorbent material at between about 0.01% and about 10% by weight of the superabsorbent material; and
a second treatment agent of polyethylene oxide powder applied to the surface of the superabsorbent material at between about 0.01% and about 10% by weight of the superabsorbent material, wherein the first treatment agent and the second treatment agent are both exposed on a surface of the superabsorbent material.

17. A method of coating superabsorbent particles, comprising:
applying a first surface treatment agent to a superabsorbent material; and
applying a second surface treatment agent to the superabsorbent material;
wherein each of the first and second surface treatment agents is exposed on a surface of the superabsorbent material.

18. The method of claim 17, wherein the first surface treatment agent comprises at least one of the group consisting of polyvinyl amine, polyquaternary ammonium, polyamine, and polyacrylic acid.

19. The method of claim 17, wherein the second surface treatment agent comprises at least one of the group consisting of a water-soluble bonding agent, a water-insoluble bonding agent, and a water-dispersible bonding agent.

20. The method of claim 17, wherein the second surface treatment agent comprises at least one of the group consisting of polyethylene oxide, polypropylene oxide, polypropylene glycol, modified cellulose, modified starch, polyethylene, polypropylene, polyester, polyamide, polystyrene, polyurethane, latex, wax, paraffin, and polyvinyl alcohol.

21. The method of claim 17, comprising applying the first surface treatment agent to the superabsorbent material in a liquid coating form, and applying the second surface treatment agent to the superabsorbent material in a powder form.

22. The method of claim 21, further comprising wetting the superabsorbent material with a solvent subsequent to applying the first surface treatment agent and prior to applying the second surface treatment agent to the superabsorbent material.

23. The method of claim 17, comprising preparing an emulsion comprising the first and second surface treatment agents and simultaneously applying the first and second surface treatment agents to the superabsorbent material by applying the emulsion to the superabsorbent material.

24. The method of claim 17, comprising using a fluidized bed process to apply the first and second surface treatment agents to the superabsorbent material.

25. The method of claim 17, comprising:
introducing the superabsorbent material into a coating chamber of a coating apparatus;
introducing a gaseous flow into the coating chamber;
spraying the first surface treatment agent into the coating chamber, wherein the first surface treatment agent is in liquid form; and
introducing the second surface treatment agent into the coating chamber, wherein the second surface treatment agent is in powder form.

26. An absorbent composition, comprising:
a superabsorbent material surface-treated with at least two different agents, wherein the at least two agents are compatible, at least one of the agents comprises a thermoplastic material, each of the at least two agents is exposed on a surface of the superabsorbent material, wherein a first of the at least two agents forms a continuous layer on the superabsorbent material, wherein a second of the at least two agents forms a discontinuous layer on the superabsorbent material, wherein at least one of the agents is chosen from polyoxides, polyalcohols, modified celluloses, polyimines, polycarboxylic acids, polyamides, polyesters, polyolefins, polystyrenes, polyurethanes, paraffin, wax, latex, copolymers, and combinations thereof, and wherein at least one of the agents is a thermally sticky agent selected from the group consisting of polyethylene oxide, polypropylene oxide, polyacrylate, polystyrene, polyamide, and combinations thereof.

27. The absorbent composition of claim 1, wherein at least one of the agents is a thermally sticky agent selected from the group consisting of polyethylene oxide, polypropylene oxide, hydroxypropyl cellulose, polyethylene imine, polyvinyl alcohol, polyethylene glycol, polyacrylate, polystyrene, polyamide, and combinations thereof.

* * * * *